(12) United States Patent
Rishi et al.

(10) Patent No.: US 10,022,071 B2
(45) Date of Patent: *Jul. 17, 2018

(54) AUTOMATIC RECOGNITION, LEARNING, MONITORING, AND MANAGEMENT OF HUMAN PHYSICAL ACTIVITIES

(71) Applicant: Khaylo Inc., San Francisco, CA (US)

(72) Inventors: Alok Rishi, Millbrae, CA (US); Arjun Rishi, Reston, VA (US); Alex Moran, San Francisco, CA (US); Niranjan Vanungare, Fremont, CA (US)

(73) Assignee: Khaylo Inc., San Francisco, CA (US)

( * ) Notice: Subject to any disclaimer, the term of this patent is extended or adjusted under 35 U.S.C. 154(b) by 412 days.

This patent is subject to a terminal disclaimer.

(21) Appl. No.: 14/621,348

(22) Filed: Feb. 12, 2015

(65) Prior Publication Data

US 2015/0224362 A1    Aug. 13, 2015

Related U.S. Application Data

(60) Provisional application No. 61/939,221, filed on Feb. 12, 2014.

(51) Int. Cl.
*A61B 5/021* (2006.01)
*A61B 5/11* (2006.01)
*G06F 19/00* (2018.01)
*A61B 5/00* (2006.01)
*A61B 5/024* (2006.01)

(52) U.S. Cl.
CPC ............ *A61B 5/1118* (2013.01); *A61B 5/1123* (2013.01); *A61B 5/7267* (2013.01); *G06F 19/3481* (2013.01); *A61B 5/021* (2013.01); *A61B 5/02438* (2013.01)

(58) Field of Classification Search
CPC ... A61B 5/021; A61B 5/1118; A61B 5/02438; G06F 19/3481
See application file for complete search history.

(56) References Cited

U.S. PATENT DOCUMENTS

| | | | |
|---|---|---|---|
| 2009/0048044 A1* | 2/2009 | Oleson | A63B 24/0062 473/570 |
| 2010/0042620 A1 | 2/2010 | Bailey et al. | |
| 2010/0141397 A1* | 6/2010 | Kim | G08B 21/0423 340/10.5 |
| 2010/0144414 A1 | 6/2010 | Edis et al. | |
| 2010/0176952 A1* | 7/2010 | Bajcsy | A61B 5/11 340/573.1 |
| 2010/0310157 A1 | 12/2010 | Kim et al. | |
| 2011/0306304 A1* | 12/2011 | Forutanpour | G06F 3/04883 455/67.11 |

(Continued)

*Primary Examiner* — Corbett B Coburn
(74) *Attorney, Agent, or Firm* — Kenealy Vaidya LLP

(57) ABSTRACT

In one embodiment, a method includes one or more processors that collect motion and physiological sensor data of a user from one or more sensors worn by the user, the sensor data comprising one or more sensor data vectors, generate an activity signature based on the sensor data, determine whether a signature match exists between the activity signature and a known activity signature associated with an activity type from a set of known activity signatures, and if the signature match exists, recognize a known activity type, otherwise if the signature match does not exist, generate an unknown activity type based on the one or more sensor data vectors.

17 Claims, 12 Drawing Sheets

(56) References Cited

U.S. PATENT DOCUMENTS

| | | | |
|---|---|---|---|
| 2012/0137795 A1 | 6/2012 | Selner | |
| 2012/0265717 A1* | 10/2012 | Narayanan | G06N 99/005 |
| | | | 706/12 |
| 2012/0283855 A1 | 11/2012 | Hoffman et al. | |
| 2013/0106684 A1 | 5/2013 | Weast et al. | |
| 2013/0262352 A1* | 10/2013 | Sung | G06N 99/005 |
| | | | 706/12 |
| 2014/0244209 A1* | 8/2014 | Lee | G06K 9/00536 |
| | | | 702/150 |
| 2015/0067699 A1* | 3/2015 | Plotkin | G06F 9/44 |
| | | | 718/107 |
| 2015/0100245 A1* | 4/2015 | Huang | A61B 5/0022 |
| | | | 702/19 |
| 2015/0193232 A1* | 7/2015 | Keal | A61B 5/1123 |
| | | | 702/150 |
| 2016/0007165 A1* | 1/2016 | Somer | H04W 4/028 |
| | | | 455/404.2 |
| 2016/0157757 A1* | 6/2016 | Murthy | A61B 5/0075 |
| | | | 600/310 |
| 2016/0342311 A1* | 11/2016 | Homick | G06F 3/04842 |
| 2017/0134511 A1* | 5/2017 | White | H04L 67/18 |
| 2017/0358242 A1* | 12/2017 | Thompson | A63B 24/0062 |
| 2018/0012242 A1* | 1/2018 | Phan | G06F 19/3475 |

\* cited by examiner

AUTOMATIC RECOGNITION, LEARNING, MONITORING, AND MANAGEMENT OF HUMAN PHYSICAL ACTIVITIES

RELATED APPLICATIONS

This application claims the benefit of U.S. Provisional Application No. 61/939,221, filed on Feb. 12, 2014, and entitled, "Automatic Recognition, Learning, Monitoring, and Management of Human Physical Activities," the contents of which are incorporated by reference as if fully set forth herein.

TECHNICAL FIELD

This disclosure generally relates to activity tracking and more specifically relates to motion and physiology sensing and analysis.

BACKGROUND

Activity trackers are devices or applications for monitoring and tracking fitness-related metrics, such as distance walked or run, calorie consumption, heartbeat, and quality of sleep. Activity trackers may be dedicated electronic monitoring devices that are synced, wirelessly or otherwise, to a computer or smartphone for long-term data tracking Activity trackers may also be independent computer or smartphone applications.

DESCRIPTION OF EXAMPLE EMBODIMENTS

Figure 1:
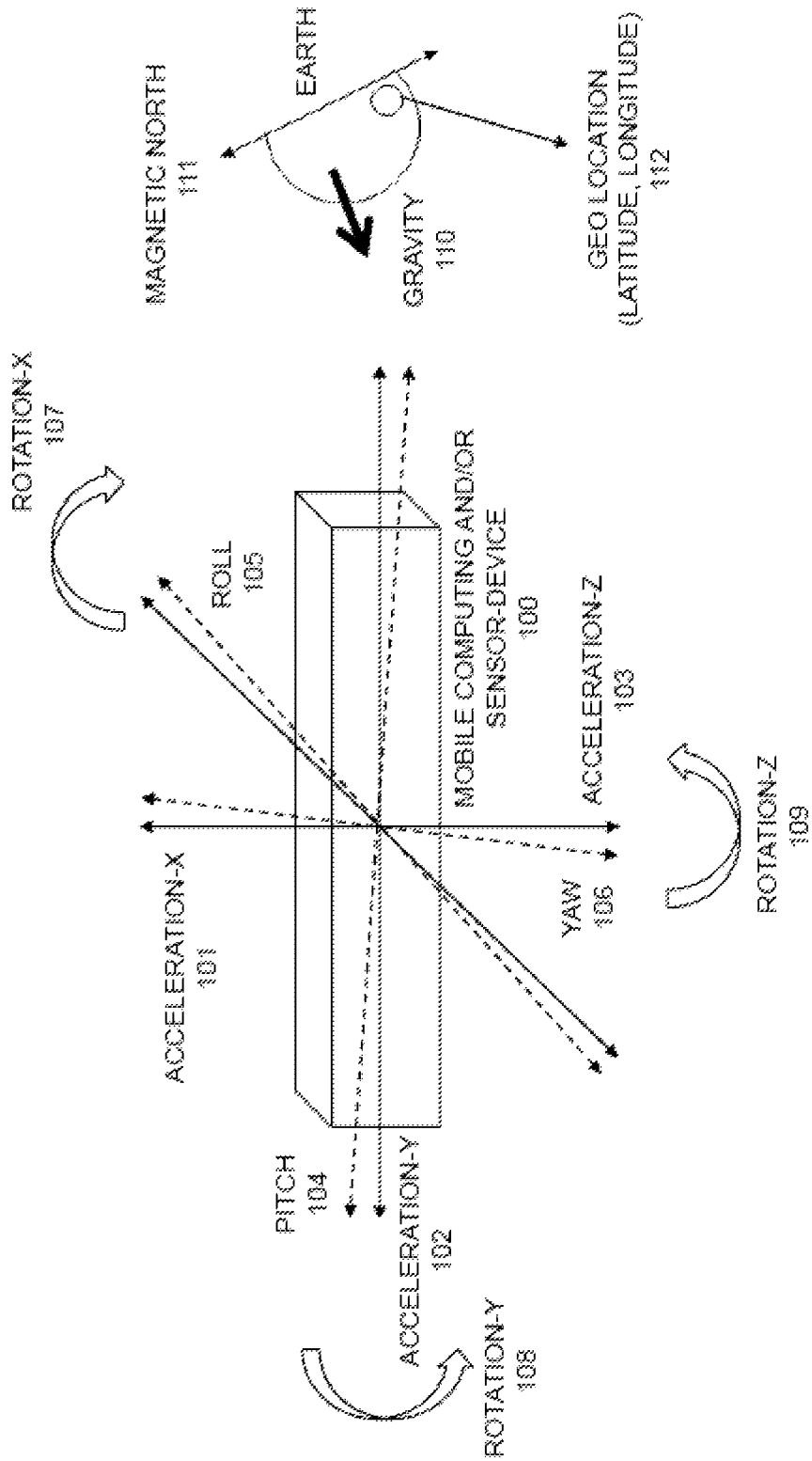
FIG. 1 illustrates example motion sensor data that may be captured by the application.

Particular embodiments comprise a set of methods, apparatus, and systems for automatically recognizing, monitoring, measuring, tracking, analyzing impact, matching domain experts or competition, recommending improvements, planning and scheduling context-aware physical human activities in areas of sports, fitness, and health are provided. The system harnesses multiple types of vector data from varied sensor-based devices, including but not limited to handheld mobile phones having or reading from one or more motion or physiological sensors. The system detects any sensor-attached human movement (for example, any periodic motion along one or more physical dimensions as measured by the motion sensor(s)) along with any available physiological readings (for example, heart-rate, calorie intake, blood pressure as measured by sensor(s)). Upon cross-correlated analyses of all such sensor data, the system derives and assigns a unique mathematical signature to the pattern of motion and any associated physiology corresponding to the physical motion routine (or workout). This set of activities (also referred to as a workout) when performed by the user, are self-detected by the system, triggering pertinent interactions within the user's social networking context, such as marking them as done on the user's social calendar, informing the user's coach or physical trainer/therapist who may have assigned the workout, of its completion status and results.

The system further extrapolates and classifies such a series of periodic motions and any associated physiology as an aggregate human activity, for example, push-ups or shoulder-stretch. The system recognizes the current activity, if its motion and physiological signature matches the signature of a previously encountered physical activity. If the system has never encountered such a sequence of physical motion and any associated physiology, the system derives a new signature and creates a new classification for this newly detected activity. By applying machine learning techniques, the system effectively learns new forms of human activities. The system derives and stores each activity's unique signature and thereby expands its repertoire of activities it may automatically detect, classify and recognize.

As the system detects activities being undertaken, it captures the performance results and completion status. Upon successful completion of the workout, the system triggers relevant social interactions within the user's social network, for example, the system marks the activity in the user's calendar and task list as completed and notifies the user's coach or physical trainer/therapist, who may have assigned the workout to the user, of the measurable performance results, along with the time and date stamp of its completion. The activity performance schedule and results are stored in a historical timeline of user's sports, fitness, and health-related activities. The system enables the user to share the results with anyone in their social network, if they so choose to do so.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

FIG. 1 depicts the types of motion sensor data that may be captured by the application per user in an example embodiment. Motion sensor data may be captured from one or more devices 100 attached to the body of the user 200 performing physical activity, for example, embedded motion tracking sensors are available in many forms, included but not limited to handheld mobile phones (when securely attached to an arm-band or waist band, for example), wrist-bands, wrist-watches, ankle-bands, knee-bands, head-band, clothing, shoes.

Examples of motion sensor data extracted and manipulated by the application include, but are not limited to: acceleration along x axis 101; acceleration along y axis 102; acceleration along z axis 103, y, z axis in 3-dimensions; pitch 104, roll 105, yaw 106, rotation along x-axis 107, rotation along y-axis 108, rotation along z-axis 109, gravitational 110 pull exerted by earth; magnetic forces exerted by earth's north 111 and south poles; and geo-location in Latitude and Longitude 112.

Figure 2:
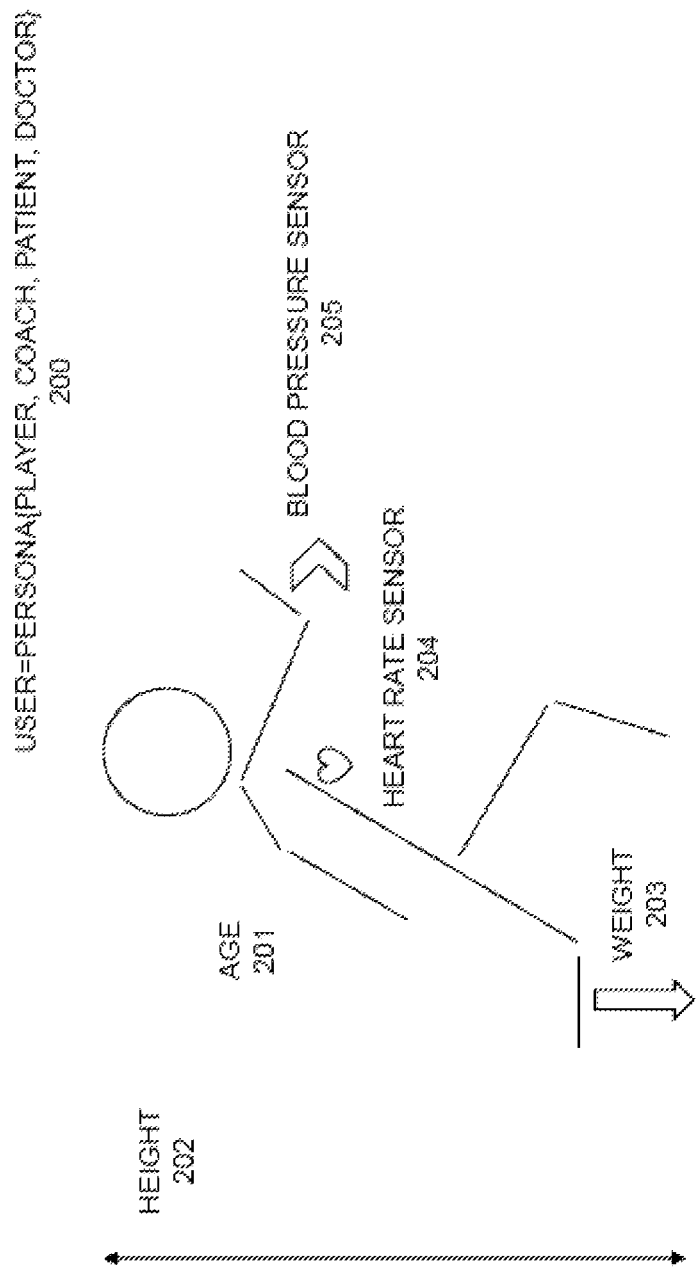
FIG. 2 illustrates example physiological sensor data that may be captured by the application.

FIG. 2 depicts the types of physiological sensor data that may be captured by the application per user in an example embodiment. Examples of physiological sensor data extracted and manipulated by the application include, but are not limited to, heart-rate 204, and blood pressure 205. Examples of physiological traits interactively gathered from the user and stored by the application include, but are not limited to, age 201, height 202, and weight 203. Additionally, examples of contextual information about the user that the application may have access to, includes but is not limited to, permanent location, permanentaddress, calendar 411, 418 of scheduled and completed activities, and the persona 200 or role that user has assumed for the time being.

Figure 3:
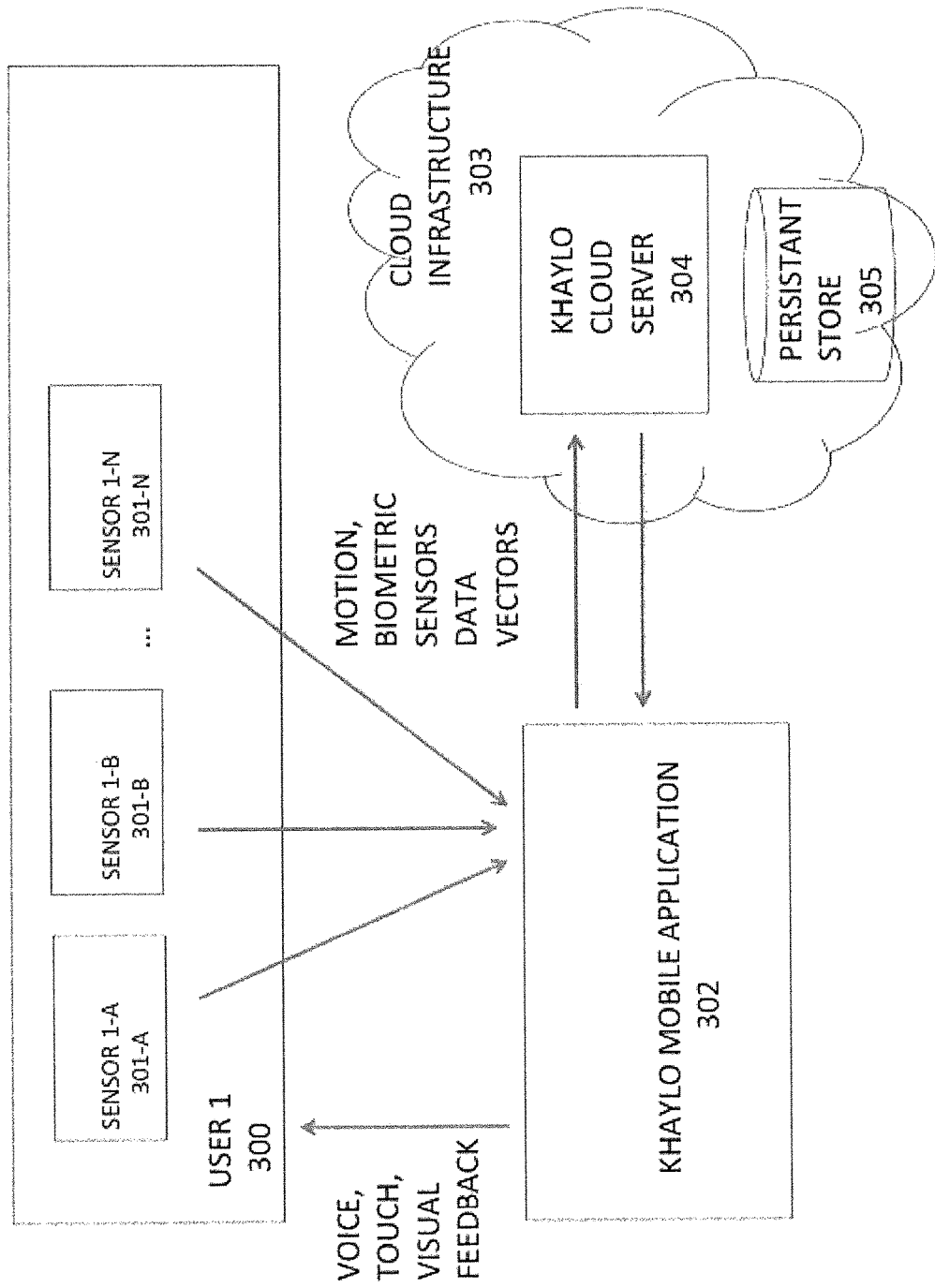
FIG. 3 illustrates an example user with one or more sensors.

FIG. 3 depicts the user 300 has on their person or embedded one or more sensor-based devices 301-A, 301-B, . . . , 301-N capable of measuring various types of motion and physiological states in an example embodiment. The user 300 also has on their person a mobile computing device 100 capable of running a mobile software application 302 that may extract, analyze, manipulate, and store any sensor data in its proximity. The mobile software application 302 communicates with its counterpart server application 304 running in a cloud infrastructure 303, over any number of wide-area-network (WAN) network protocols over transports, including but not limited to HTTPS over TCP/IP. The server application 304 may read-write data to and from a persistent store, such as a fast-object-dictionary-based database, for example.

The mobile software application 302, upon extracting, manipulating, and analyzing the sensor data vectors, may provide results and feedback to the user via any number of user interfaces such as voice, touch, visual feedback mechanisms. In a context-aware manner, the mobile software application 302 may analyze, recognize, learn, measure results of the user's activities from sensor data vectors, while managing user's schedule of activities and providing real time feedback and notifications to the user and anyone the user has given permission to view, within the user's social network, sports network, fitness network, or health network.

Figure 4:
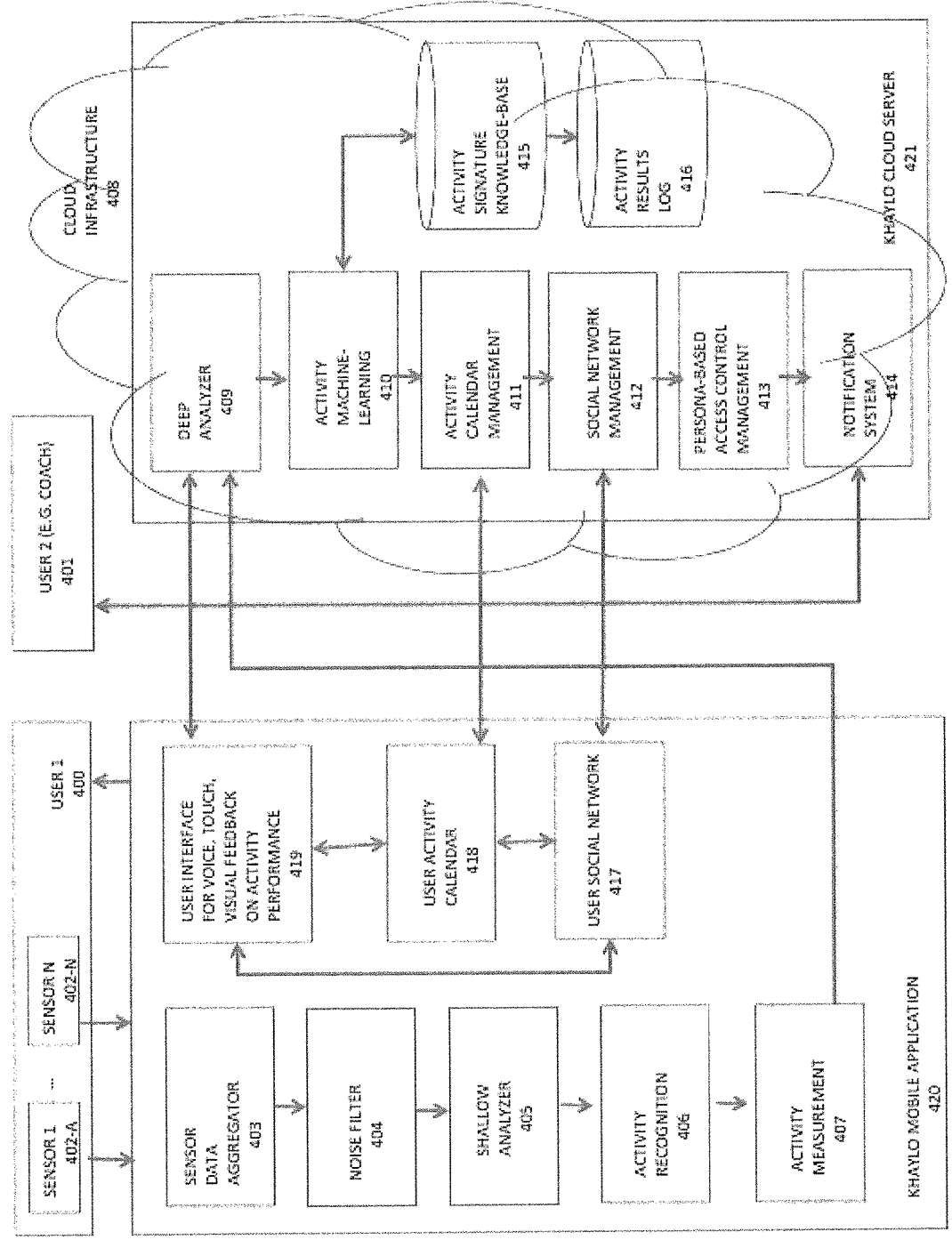
FIG. 4 illustrates an example sensor system.

FIG. 4 illustrates an example method, including the underlying software and hardware computational components, required to achieve the above goals. As shown, Sensor 1 402a to Sensor N 402n capture data from the user that the user has authorized it to extract, manipulate, analyze, monitor, and store. The data is captured by any one or more of a mobile phone sensor, wrist-band sensor, heart-rate monitor sensor, or any sensor of the user's movement and physiological activity.

Mobile application 420 includes sensor data aggregator 403 that collects the data captured from the sensors by recording data vectors from the sensors. In some embodiments, a few seconds of data vectors are collected from sensors 402a to 402n. In some embodiments, noise filter 404 from the mobile application filters noisy data from the collected data.

Shallow analyzer 405 on mobile application 420 performs a first-pass, quick and shallow analysis of the collected data. In some embodiments, shallow analyzer 405 performs statistical analysis on each data vector to calculate the mean, average deviation, standard deviation, variance, wave amplitude, length, frequency, distance of the incoming data vectors. Shallow analyzer 405 assigns a unique number based on the analysis to generate a unique mathematical signature for collected data as the signature for the user's activity. An activity recognition 406 process analyzes the mathematical signature by a vector quantization process, such as a K-MEANS process, to attempt to assign the mathematical signature into an existing cluster having a signature. If the assigning is successful, the shallow analyzer 405 has found an activity match between the user's activity and a known activity.

All the data vectors and the shallow analysis results are sent to the server application 421 in the cloud for further analyses. In some embodiments, the data vectors and the shallow analysis results are sent to deep analyzer 409 for further processing at the server application 421. In some embodiments, when shallow analyzer 405 fails to match the activity signature to a known activity, the data vectors and the shallow analysis results are sent to a machine-learning module for creating a new activity classification, signature, and profile for the activity that the data vectors represent.

Deep analyzer 409 further provides feedback to user interface 419 on the mobile application 420, such as sending the new activity profile and signature to be cached onto the mobile application, for application in any future shallow analysis, indicating to the user via the user interface, speech, touch, text, visual, that the system could not recognize this activity and allowing the user to create a new speech or text tag for this activity. The user-defined tag is transmitted to the server application for storage into the persistent activity knowledgebase 415 and updated profile. Server 421 may also include activity results tog 416 for logging the activity types identified by the user.

Activity measurement 407 is performed based on additional data collected. The data is analyzed to measure units of the activity's progression, corresponding to repeated cycles within the motion and physiological state changes.

Server 421 includes activity calendar management that communicates with the user activity calendar 418 on the mobile application 420, for example, to mark a scheduled activity as completed. Server 421 includes social network management 412 which communicates with a user's social network, sports network, fitness network, or health network interfaces on mobile application 420.

Server 421 includes a persona-based access control management 413, which allows a second user, such as user 401, to assume a persona for the user, such as a coach persona or a doctor persona. A user's personas are granted access to particular user data, including any data generated from user activity recognition 406 and user activity measurement 407. In some embodiments, the user's personas receive notifications from notification system 414.

Regarding FIGS. 5-9, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with some embodiments, occur in a different order and concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with some embodiments.

Figure 5:
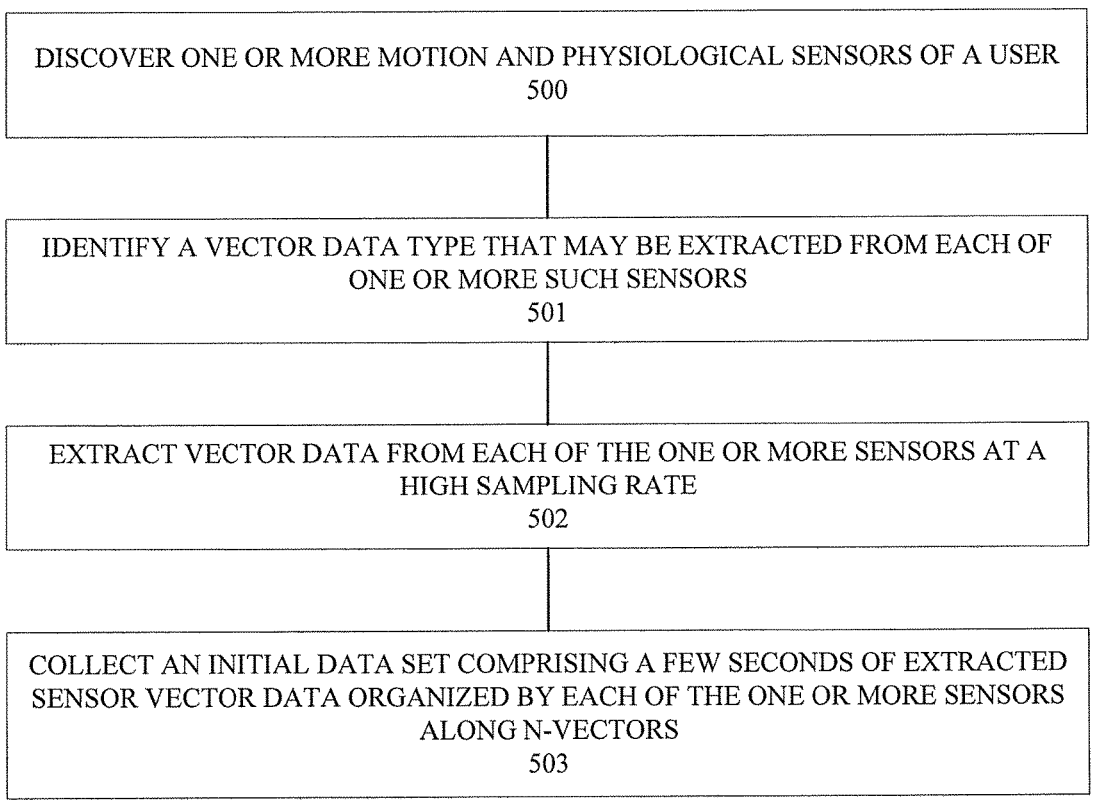
FIG. 5 illustrates an example method of discovering and extracting data from one or more sensors.

FIG. 5 illustrates an example method process to discover and extract data from one or more sensors on the person of the user using a mobile application running on a mobile computational device on the person of the user. For example, sensor data being captured by a mobile phone, wrist-band, heart-rate monitor may be gathered by the mobile application over a network such as TCP/IP, Bluetooth, wireless. In step 500, the mobile application discovers all available sensors from which the user has authorized it to extract, manipulate, analyze, monitor, and store sensor data. In step 501, identify all available data vector types, for example, heart-rate, acceleration along x, y, z axis and others. In step 502, lookup user preference from the persistent store and check their preference for automatic monitoring of activities or manual/user-initiated start of monitoring of activities. Based on the user preference and upon detection of motion and physiological state changes from sensors, either automatically start recording data vectors or present the user with the appropriate user interface, for example, a start activity monitoring button, to initiate such activity monitoring and analyses. Set the data sampling rate to high frequency, heuristically set per user/activity, to, for example, collect data every 1/60th of a second. The system needs to make a quick assessment of the type and measure of user activity by closely looking at fine grain data samples at the beginning of any activity cycle. High sampling rate ensures more accurate activity classification and measurement. In step 503, collect a few seconds of data vectors. This step prepares data before it may be sent for shallow analysis.

Figure 6:
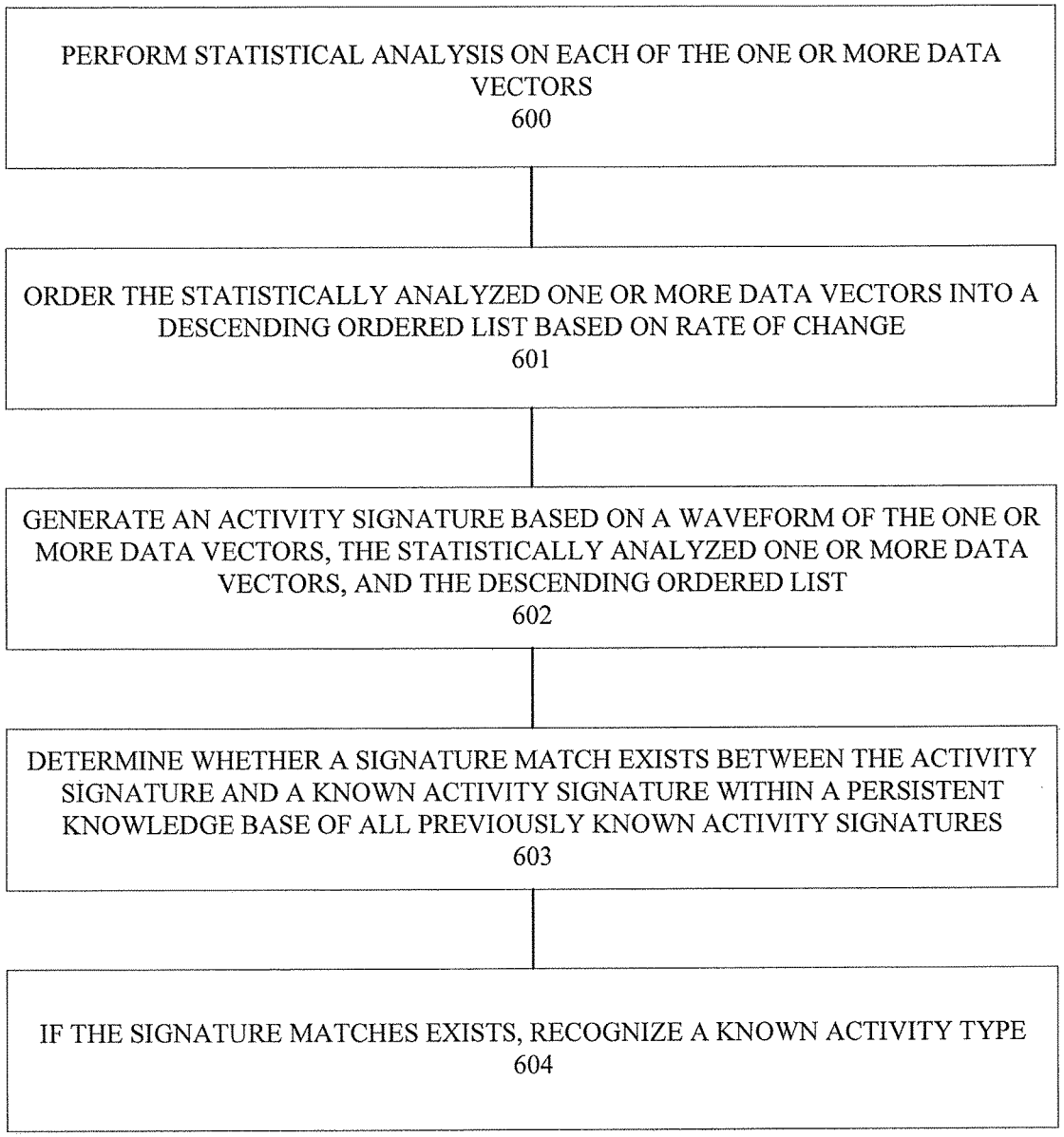
FIG. 6 illustrates an example method of analyzing data real-time without invoking a network server.

FIG. 6 illustrates an example method for performing a first-pass, quick and shallow analysis i.e. real time analysis on board the mobile device itself, without having to invoke the server application across the wide area network, according to some embodiments. In step 600, perform statistical analysis on each data vector to calculate the mean, average deviation, standard deviation, variance, wave amplitude, length, frequency, distance of the incoming data vectors. This provides insight into the rate of change occurring within each data vector. In step 601, the process orders each data vector into a stack-ranked, descending order of rate of change. This steps yields the order of data vector where most motion or physiological state changes are occurring. These are the dominant forces of change within the user's current activity. In step 602, the process assigns a unique mathematical sequence of numbers, based on the ordered list of data vectors, denoting the unique mathematical signature, from highest-order bits to lowest-ordered bits. This constitutes the signature of the activity that the user is performing. In step 603, the process matches this sequence of numbers or bits, also what we are referring to as activity signature, with existing, known activity signatures, as described within the activity profile. The activity profile also contains a heuristic feature for an allowable margin of error.

The process then pushes the data vectors into a vector quantization process, such as a K-MEANS process, that takes the incoming data vectors' signature and tries to assign it to the closest cluster of known activities. If the algorithm is able to, in successive iterations, settle on a match, that is assign the new data vectors into an existing cluster with similar signature, then system has found an activity match. In step 604, in the event of a successful match, classify and tag the incoming data vectors with the profile information of the known matching activity. The mobile application indicates to the user via the user interface of the mobile application, via voice, text, visual, touch vibration, that the activity was successfully identified, along with its tag name, for example: "you are doing pushups."

Figure 7:
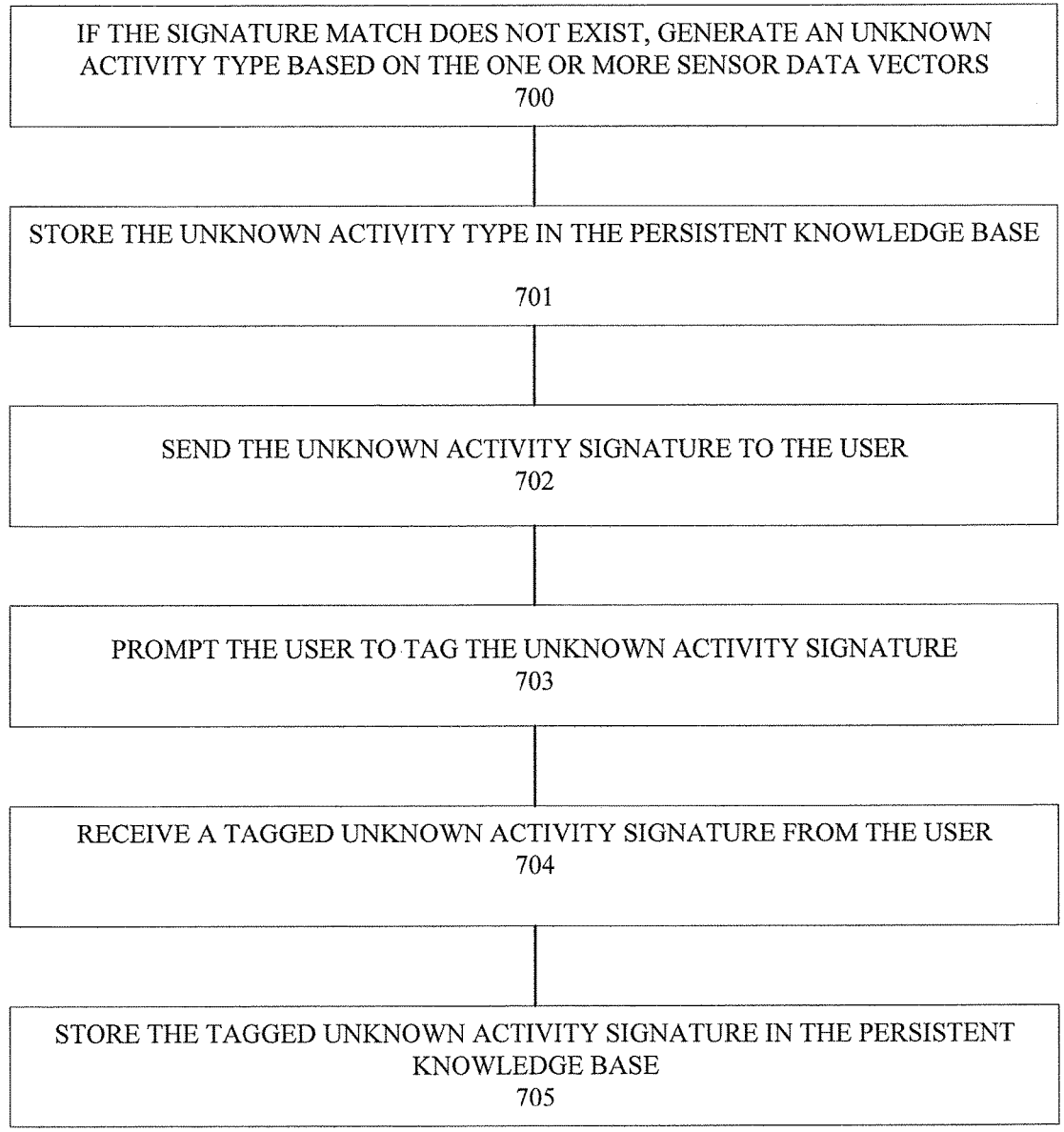
FIG. 7 illustrates an example method of analyzing data by invoking a network server.

FIG. 7 illustrates an example method for performing a second-pass, deep analysis of this unknown activity. In step 700, all the data vectors and the shallow analysis results are sent to the server application in the cloud for further analyses. This data is packaged and sent into the K-MEANS training algorithm, so it may create a new activity classification, signature, and profile for the activity that the data vectors represent. In step 701, this new information about the newly classified activity is stored in the persistent knowledgebase of previously known activities. In step 702, the server application sends the new activity profile and signature to be cached onto the mobile application, for application in any future shallow analysis. In step 703, the mobile application indicates to the user via the user interface, speech, touch, text, visual, that the system could not recognize this activity and allows the user to create a new speech or text tag for this activity. In steps 704 and 705, this user-defined tag is transmitted to the server application for storage into the persistent activity knowledgebase and updated profile.

Figure 8:
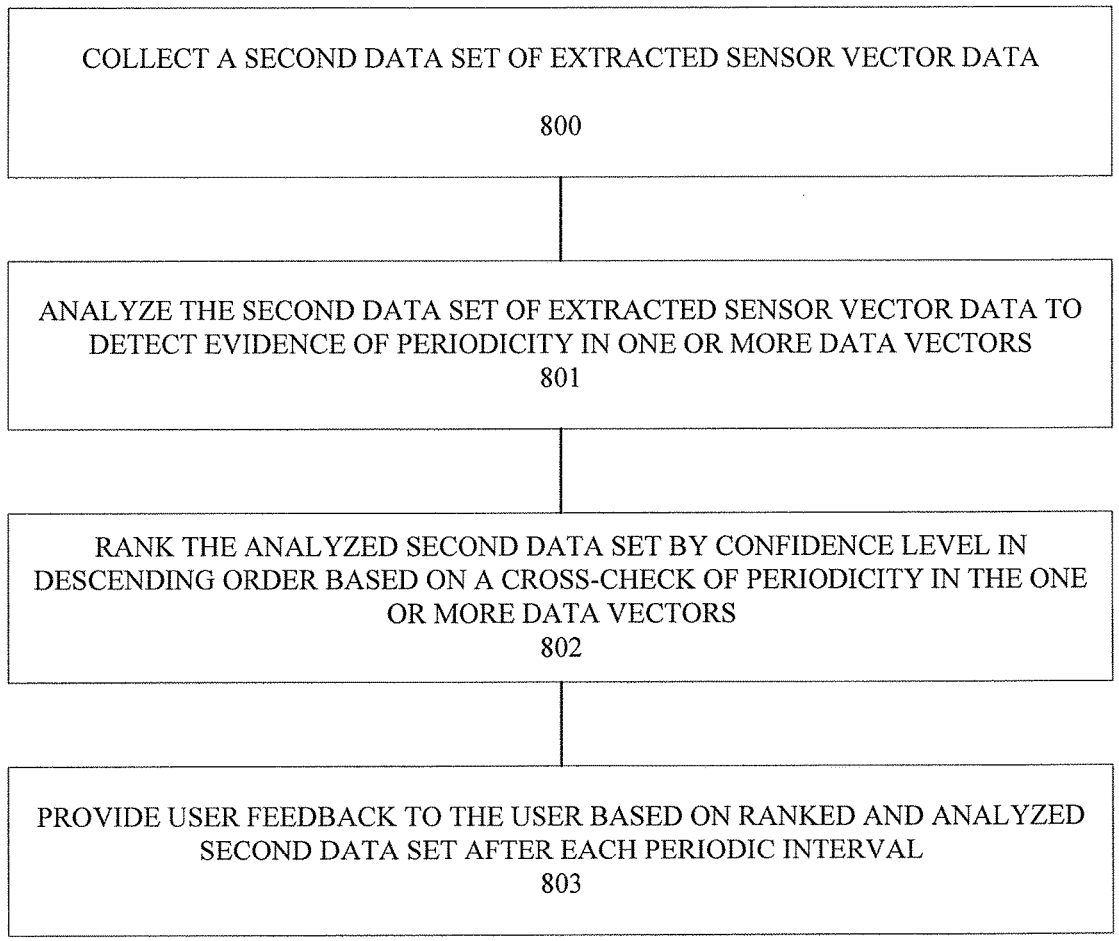
FIG. 8 illustrates an example method of counting units of an activity's progression.

FIG. 8 illustrates an example method for counting or measuring units of the activity's progression, corresponding to the repeating cycles within the motion and physiological state changes. In step 800, a second data set is collected comprising further extracted sensor vector data. In step 801, and once the activity type has been determined or derived, all available data vectors, include the second data set of extracted sensor vector data, may be analyzed to detect evidence of periodicity in one or more of the data vectors. In particular embodiments, one or more of three methods are suggested but not limited to, as examples, to detect periods, that is, cycles, within the activity and along any one or more of the data vectors. In particular embodiments, adaptive activity monitoring using cosine similarity method may be used, where the cosine similarity is calculated between current data vectors and baseline data vectors. In particular embodiments, wave amplitude, length, period, frequency of each data vector may be calculated and mapped into wave semantics. In particular embodiments, frequencies from a Fast Fourier Transform of the data vector may be calculated. In particular embodiments, a confidence level may be assigned to each result based on particular error margins.

This process begins with creating a profile for each activity by applying statistical techniques such as Least Squares to training data, to produce a model for each activity. The next step is to implement the model on the monitoring platform. A profile is also created on the service based web platform wherein the model's coefficient parameters are stored and may be updated. The final step in the process is the use of sensor data from the monitoring platform to update the model's parameters that are specific to the client and user of the application.

The profile creation step is a pre-process step to the monitoring of a client, and is performed in the research and development phase of application development. A significant amount of data must be acquired to create an accurate model of the activity to be monitored. The data is then fit with an equation for each input dimension that is able to be monitored.

In step 802, results of the analysis of frequency and count of the second data set may be cross-checked based on margins of tolerable errors per activity, as defined in the activity profile, and ranked by confidence level results from methods of analyzing and counting described above. In step 803, provide real-time feedback to the user of the activity count, via voice, visual, text interfaces, with each periodic interval of repetition.

Figure 9:
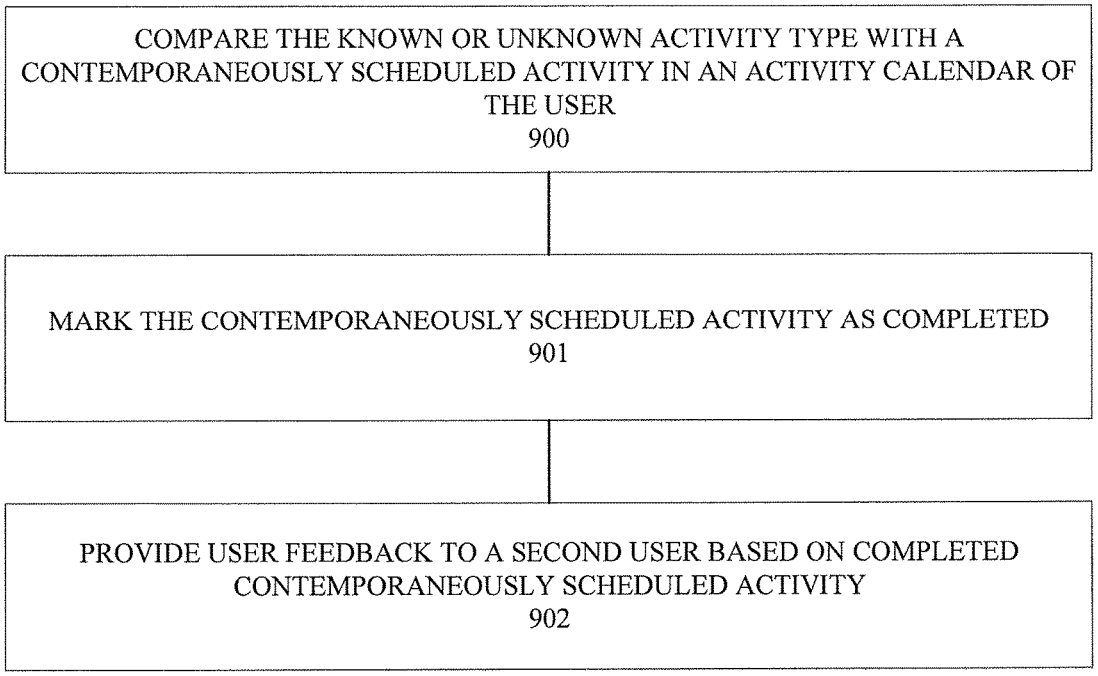
FIG. 9 illustrates an example method for managing a user's activity schedule.

FIG. 9 illustrates an example method for managing a user's activity schedule in a calendar and informing interested and authorized parties of the completion of an activity by the user. In step 900, upon completion of a set of activities, check the user's activity schedule in their calendar and match against any pending activity schedule. A set of activities may include, for example, pushups, crunches, and any other physical activity. A set of activities, including workouts, may have been scheduled by the user's coach, personal trainer, physical therapist, and any such valid player-trainer or patient-doctor relationship that the user may have in their social network. In step 901, if the date, time, and activity type matches with what is in the user's calendar then mark the scheduled activity as completed in the user's calendar. In particular embodiments, results, such as calories burned, distance covered, speed, and exercise counts may also be loaded into the user's calendar when the scheduled activity is marked as completed. In step 902, if such a match was found, then send notification of the activity completion and results to the assignor of the activity, including a second user, for example, the user's coach, physical therapist, trainer, and doctor, which are personas that other users within the social, sports, fitness, health network may assume and the user has a valid relationship with the other user, in the capacity of the persona, and has authorized dissemination of such information to them. In particular embodiments, the assignor may be allowed to comment on the user's results within the user's workout event on the calendar.

Figure 10:
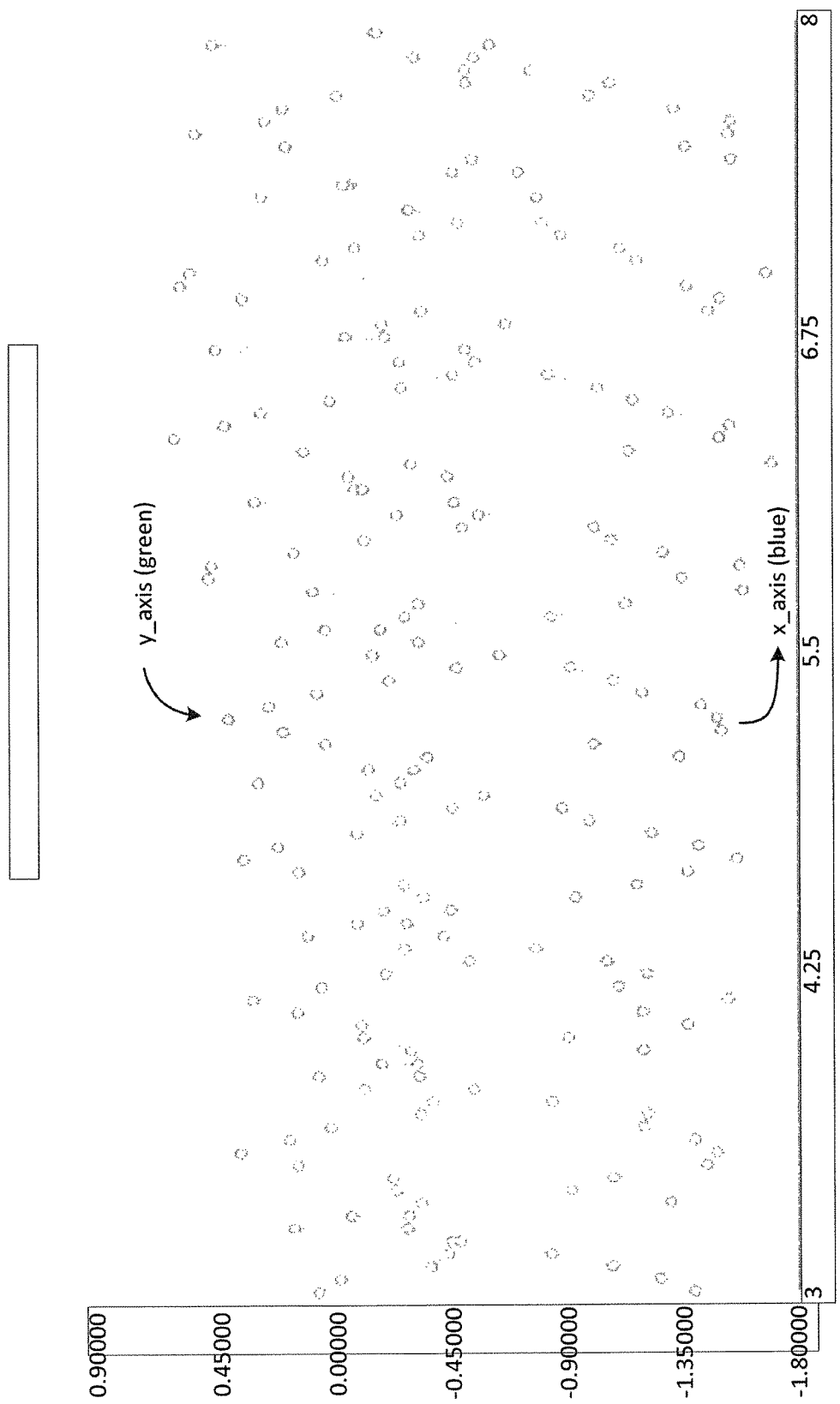
FIG. 10 illustrates an example set of two sample vectors of incoming data.

FIG. 10 depicts an exemplary process to analyze two sample vectors of incoming data. Next, the model must be implemented on the monitoring device or any computer system that is capable of gathering data from the monitoring device. The computer system must be capable of composing the model from real time sensor data and computing its output. The first step in the computation is the comparison of real time sensor data to a threshold matrix. The output of this step is the model to be used. Once the model is selected and computed, its output is presented to the client and to the service platform.

Finally, as the client continues to use the monitoring device, the model's coefficient parameters that are specific to the client are progressively updated. The coefficients are updated by values proportional to the distance the model's output vector is from the client's recorded performance vector. Provided the distance is small enough not to abort the monitoring phase or to trigger an alternate model through the threshold matrix, the coefficients will be updated in real time. In the case where the threshold matrix or the chosen activity model do not fit the client's individual activity profile, or activity has not yet been profiled, then the client will be presented with the option to record a new profile for that activity, which will trigger the beginning of the process.

Figure 11:
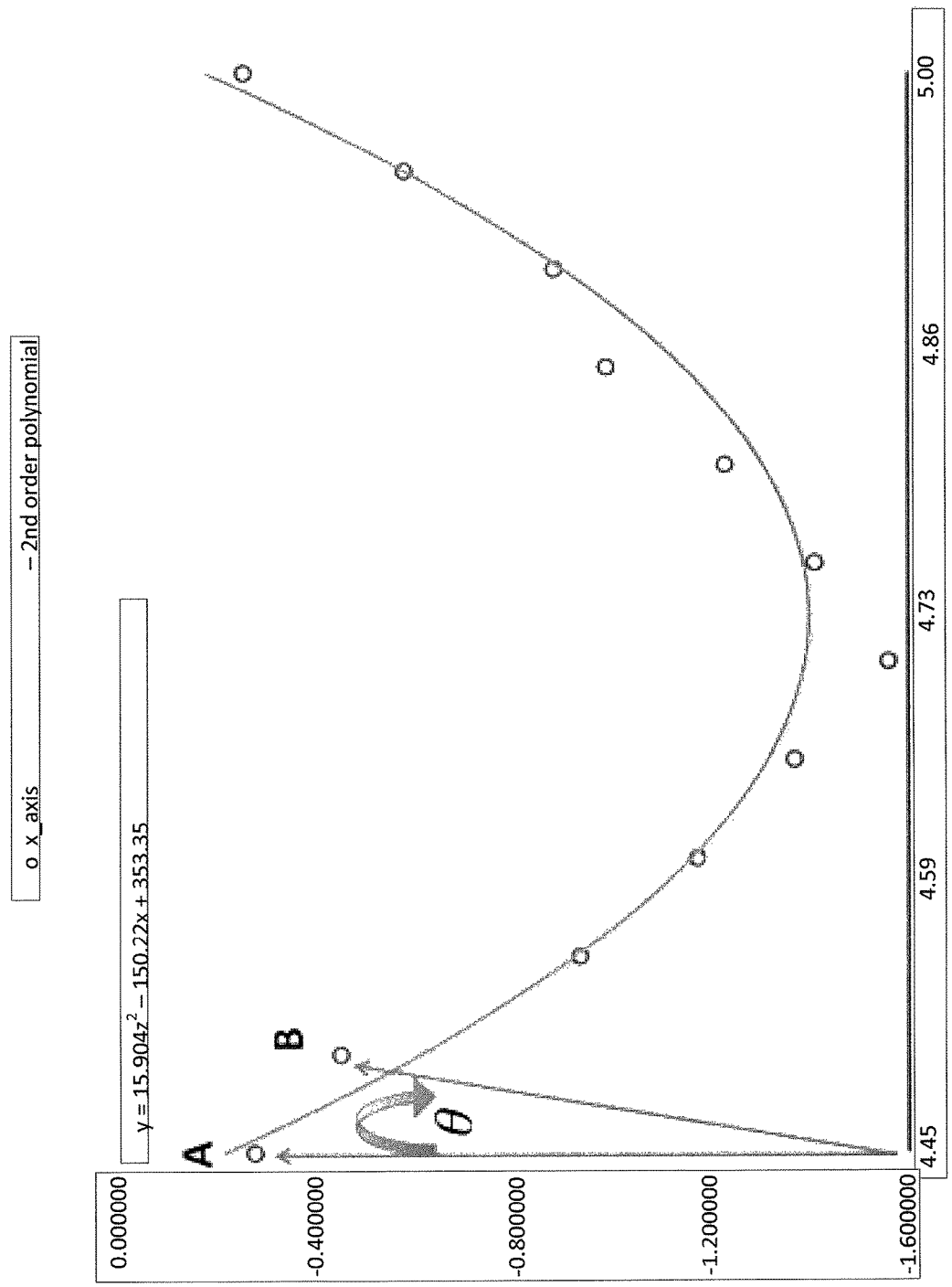
FIG. 11 illustrates an example second order polynomial whereby the distance between two vectors is calculated using cosine similarity.

FIG. 11 depicts an example second order polynomial whereby the distance between two vectors is calculated using cosine similarity. In particular embodiments, a distance (theta, θ) between two vectors (A and B) may be calculated using cosine similarity between current data vectors and an established baseline vector of the similar activity. The number of occurrences where the cosine similarity between baseline and current vectors is considered a match may then be counted, which provides the cyclical count of repeating motion or physiological state changes. In an example method of calculating the distance between two vectors using cosine similarity, Map data vectors may be mapped into wave form, the polynomial equation the defines the shape of the wave may be derived The amplitude, frequency, period, may then be counted in order to count the number of oscillations of the wave, which then may denote a count of repeating cycles within an activity. Histogram/frequency of the high order data vectors may be calculated by applying a Fast Fourier Transform (FFT) to the incoming data vectors.

Figure 12:
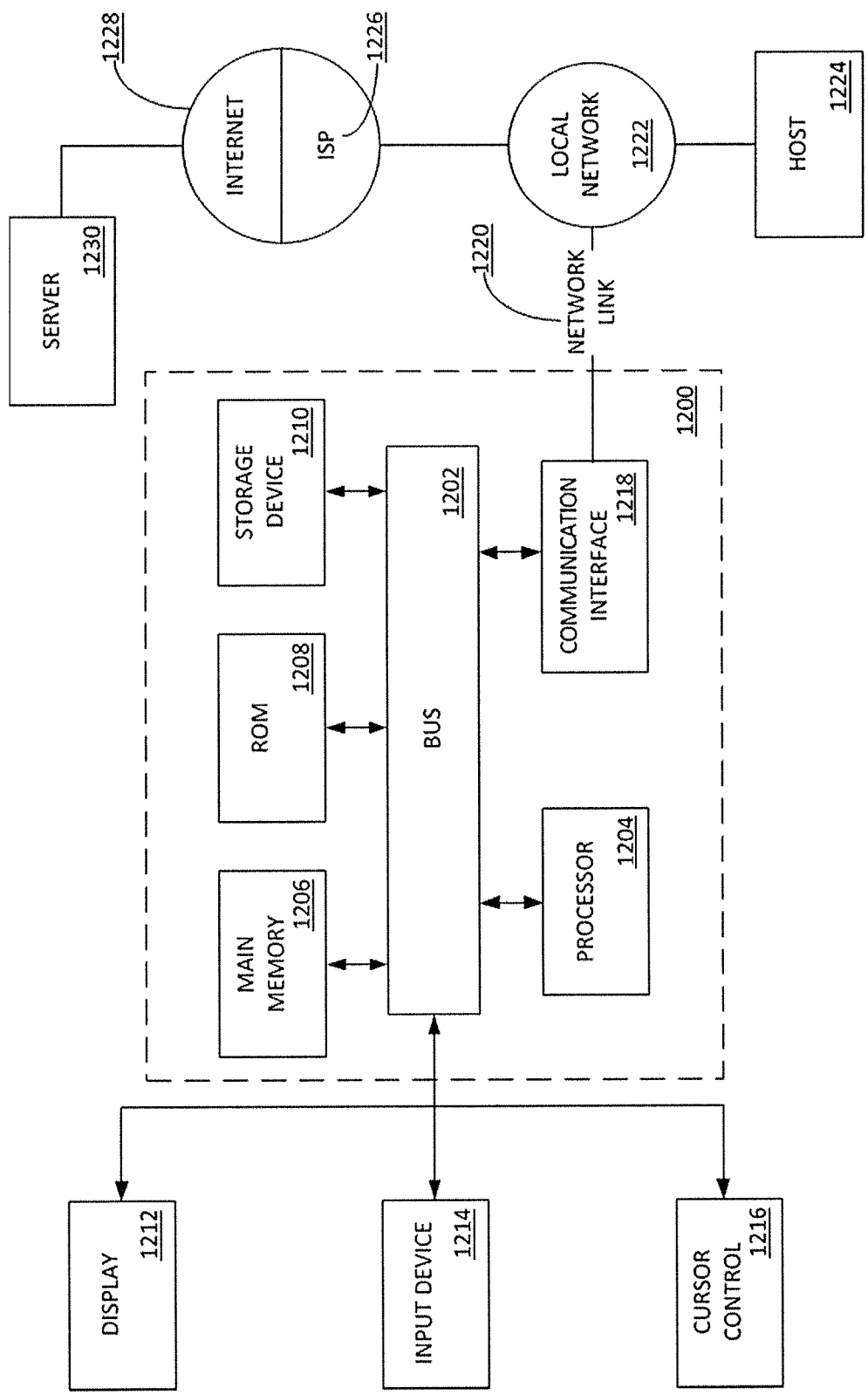
FIG. 12 illustrates an example computer system.

FIG. 12 is a block diagram that illustrates a computer system 1200 upon which some embodiments may be implemented. Computer system 1200 includes a bus 1202 or other communication mechanism for communicating information, and a processor 1204 coupled with bus 1202 for processing information. Computer system 1200 also includes a main memory 1206, such as a random access memory (RAM) or other dynamic storage device, coupled to bus 1202 for storing information and instructions to be executed by processor 1204. Main memory 1206 also may be used for storing temporary variables or other intermediate information during execution of instructions to be executed by processor 1204. Computer system 1200 further includes a read only memory (ROM) 1208 or other static storage device coupled to bus 1202 for storing static information and instructions for processor 1204. A storage device 1210, such as a magnetic disk, optical disk, or a flash memory device, is provided and coupled to bus 1202 for storing information and instructions.

Computer system 1200 may be coupled via bus 1202 to a display 1212, such as a cathode ray tube (CRT) or liquid crystal display (LCD), for displaying information to a computer user. An input device 1214, including alphanumeric and other keys, is coupled to bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane. In some embodiments, input device 1214 is integrated into display 1212, such as a touchscreen display for communication command selection to processor 1204. Another type of input device includes a video camera, a depth camera, or a 12D camera. Another type of input device includes a voice command input device, such as a microphone operatively coupled to speech interpretation module for communication command selection to processor 1204.

Some embodiments are related to the use of computer system 1200 for implementing the techniques described herein. According to some embodiments, those techniques are performed by computer system 1200 in response to processor 1204 executing one or more sequences of one or more instructions contained in main memory 1206. Such instructions may be read into main memory 1206 from another machine-readable medium, such as storage device 1210. Execution of the sequences of instructions contained in main memory 1206 causes processor 1204 to perform the process steps described herein. In alternative embodiments, hard-wired circuitry may be used in place of or in combination with software instructions to implement the invention. Thus, embodiments are not limited to any specific combination of hardware circuitry and software. In further embodiments, multiple computer systems 1200 are operatively coupled to implement the embodiments in a distributed system.

The terms "machine-readable medium" as used herein refer to any medium that participates in providing data that causes a machine to operate in a specific fashion. In an embodiment implemented using computer system 1200, various machine-readable media are involved, for example, in providing instructions to processor 1204 for execution. Such a medium may take many forms, including but not limited to storage media and transmission media. Storage media includes both non-volatile media and volatile media. Non-volatile media includes, for example, optical disks, magnetic disks, or flash memory devices, such as storage device 1210. Volatile media includes dynamic memory, such as main memory 1206. Transmission media includes coaxial cables, copper wire and fiber optics, including the wires that comprise bus 1202. Transmission media may also take the form of acoustic or light waves, such as those generated during radio-wave and infra-red data communications. All such media must be tangible to enable the instructions carried by the media to be detected by a physical mechanism that reads the instructions into a machine.

Common forms of machine-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, flash memory device, any other memory chip or cartridge, a carrier wave as described hereinafter, or any other medium from which a computer may read.

Various forms of machine-readable media may be involved in carrying one or more sequences of one or more instructions to processor 1204 for execution. For example, the instructions may initially be carried on a magnetic disk of a remote computer. The remote computer may load the instructions into its dynamic memory and send the instructions over a data transmission line using a modem. A modem local to computer system 1200 may receive the data on the data transmission line and use an infra-red transmitter to convert the data to an infra-red signal. An infra-red detector may receive the data carried in the infra-red signal and appropriate circuitry may place the data on bus 1202. Bus 1202 carries the data to main memory 1206, from which processor 1204 retrieves and executes the instructions. The instructions received by main memory 1206 may optionally be stored on storage device 1210 either before or after execution by processor 1204.

Computer system 1200 also includes a communication interface 1218 coupled to bus 1202. Communication interface 1218 provides a two-way data communication coupling to a network link 1220 that is connected to a local network 1222. For example, communication interface 1218 may be an integrated services digital network (ISDN) card or other internet connection device, or a modem to provide a data communication connection to a corresponding type of data transmission line. As another example, communication interface 1218 may be a local area network (LAN) card to provide a data communication connection to a compatible LAN. Wireless network links may also be implemented. In any such implementation, communication interface 1218 sends and receives electrical, electromagnetic or optical signals that carry digital data streams representing various types of information.

Network link 1220 typically provides data communication through one or more networks to other data devices. For example, network link 1220 may provide a connection through local network 1222 to a host computer 1224 or to data equipment operated by an Internet Service Provider (ISP) 1226. ISP 1226 in turn provides data communication services through the world wide packet data communication network now commonly referred to as the Internet 1228. Local network 1222 and Internet 1228 both use electrical, electromagnetic or optical signals that carry digital data streams. The signals through the various networks and the signals on network link 1220 and through communication interface 1218, which carry the digital data to and from computer system 1200, are exemplary forms of carrier waves transporting the information.

Computer system 1200 may send messages and receive data, including program code, through the network(s), network link 1220 and communication interface 1218. In the Internet example, a server 1230 might transmit a requested code for an application program through Internet 1228, ISP 1226, local network 1222 and communication interface 1218.

The received code may be executed by processor 1204 as it is received, and stored in storage device 1210, or other non-volatile storage for later execution. In this manner, computer system 1200 may obtain application code in the form of a carrier wave.

Although the present embodiments have been described with reference to specific example embodiments, various modifications and changes may be made to these embodiments without departing from the broader spirit and scope of the various embodiments. For example, the various devices, modules, etc. described herein may be enabled and operated using hardware circuitry, firmware, software or any combination of hardware, firmware, and software (e.g., embodied in a machine-readable medium).

In addition, it will be appreciated that the various operations, processes, and methods disclosed herein may be embodied in a machine-readable medium and a machine accessible medium compatible with a data processing system (e.g., a computer system), and may be performed in any order (e.g., including using means for achieving the various operations). Accordingly, the specification and drawings are to be regarded in an illustrative rather than a restrictive sense. In some embodiments, the machine-readable medium may be a non-transitory form of machine-readable medium.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

What is claimed is:

1. A processor implemented method of performing motion and physiology sensing and analysis, the method being implemented by one or more processors and one or more sensors to perform the following operations:

sense motion and physiological sensor data of a user from the one of more sensors worn by the user;

collect the motion and physiological sensor data of the user from the one or more sensors worn by the user, the sensor data including one or more sensor data vectors;

generate an activity signature based on the sensor data;

determine whether a signature match exists between the activity signature and a known activity signature associated with an activity type from a set of known activity signatures, such that:

if the signature match exists, recognize a known activity type; and if the signature match does not exist, generate an unknown activity type based on the one or more sensor data vectors;

compare the known or unknown activity type with a contemporaneously scheduled activity in an activity calendar of the user; and mark the contemporaneously scheduled activity as completed.

2. The method of claim 1, wherein determine whether a signature match exists comprises performing a vector quantization process on the activity signature.

3. The method of claim 1, further comprising classify the unknown activity type for future matching.

4. The method of claim 1, wherein generate an unknown activity type comprises machine learning techniques.

5. The method of claim 1, further comprising provide user feedback to the user based on the known activity type or the unknown activity type.

6. The method of claim 1, further comprising provide user feedback to the user based on the known activity type or the unknown activity type in a context-aware manner.

7. The method of claim 6, wherein the context-aware manner comprises a social network, sports network, fitness network, or health network.

8. The method of claim 1, further comprising provide user feedback to a second user based on the completed contemporaneously scheduled activity.

9. A system configured to perform motion and physiology sensing and analysis, the system comprising:
one or more sensors worn by a user configured to sense motion and physiological sensor data of the user; and
one or more processors operable to:
collect the motion and physiological sensor data of the user from the one or more sensors worn by the user, the sensor data including one or more sensor data vectors;
generate an activity signature based on the sensor data;
determine whether a signature match exists between the activity signature and a known activity signature associated with an activity type from a set of known activity signatures, such that:
if the signature match exists, recognize a known activity type; and
if the signature match does not exist, generate an unknown activity type based on the one or more sensor data vectors;
compare the known or unknown activity type with a contemporaneously scheduled activity in an activity calendar of the user; and
mark the contemporaneously scheduled activity as completed.

10. The system of claim 9, further comprising classify the unknown activity type for future matching.

11. The system of claim 9, further comprising provide user feedback to the user based on the known activity type or the unknown activity type.

12. The system of claim 9, further comprising provide user feedback to the user based on the known activity type or the unknown activity type in a context-aware manner.

13. The system of claim 9, further comprising provide user feedback to a second user based on the completed contemporaneously scheduled activity.

14. One or more computer-readable non-transitory storage media embodying software that is operable for use with one or more sensors worn by a user configured to sense motion and physiological sensor data of the user to perform motion and physiology sensing and analysis by executing the following operations:
collect motion and physiological sensor data of the user from the one or more sensors worn by the user, the sensor data including one or more sensor data vectors;
generate an activity signature based on the sensor data;
determine whether a signature match exists between the activity signature and a known activity signature associated with an activity type from a set of known activity signatures, such that:
if the signature match exists, recognize a known activity type; and
if the signature match does not exist, generate an unknown activity type based on the one or more sensor data vectors;
compare the known or unknown activity type with a contemporaneously scheduled activity in an activity calendar of the user; and
mark the contemporaneously scheduled activity as completed.

15. The media of claim 14, further comprising classify the unknown activity type for future matching.

16. The media of claim 14, further comprising provide user feedback to the user based on the known activity type or the unknown activity type.

17. The media of claim 14, further comprising provide user feedback to the user based on the known activity type or the unknown activity type in a context-aware manner.

* * * * *